(12) United States Patent
Buyuktimkin et al.

(10) Patent No.: US 10,588,873 B2
(45) Date of Patent: *Mar. 17, 2020

(54) TOPICAL ANTIFUNGAL COMPOSITIONS

(71) Applicant: Exodos Life Sciences LP, Durham, NC (US)

(72) Inventors: Servet Buyuktimkin, San Diego, CA (US); Nadir Buyuktimkin, San Diego, CA (US); James L. Yeager, Lake Forest, IL (US)

(73) Assignee: Exodos Life Sciences LP, Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/255,271

(22) Filed: Jan. 23, 2019

(65) Prior Publication Data

US 2019/0151260 A1    May 23, 2019

Related U.S. Application Data

(63) Continuation-in-part of application No. 15/760,390, filed as application No. PCT/US2016/055978 on Oct. 7, 2016, now Pat. No. 10,272,054.

(60) Provisional application No. 62/238,464, filed on Oct. 7, 2015.

(51) Int. Cl.
| | | |
|---|---|---|
| *A61K 31/137* | (2006.01) |
| *A61K 31/5375* | (2006.01) |
| *A61K 31/454* | (2006.01) |
| *A61K 9/00* | (2006.01) |
| *A61K 47/36* | (2006.01) |
| *A61K 47/14* | (2017.01) |
| *A61K 47/10* | (2017.01) |
| *A61K 47/12* | (2006.01) |
| *A61K 9/06* | (2006.01) |

(52) U.S. Cl.
CPC .......... *A61K 31/137* (2013.01); *A61K 9/0014* (2013.01); *A61K 9/06* (2013.01); *A61K 31/454* (2013.01); *A61K 31/5375* (2013.01); *A61K 47/10* (2013.01); *A61K 47/12* (2013.01); *A61K 47/14* (2013.01); *A61K 47/36* (2013.01)

(58) Field of Classification Search
None
See application file for complete search history.

(56) References Cited

U.S. PATENT DOCUMENTS 10,272,054 B2 * 4/2019 Buyuktimkin ....... A61K 31/137

* cited by examiner

*Primary Examiner* — Brian J Davis
(74) *Attorney, Agent, or Firm* — Olson & Cepuritis, Ltd.

(57) ABSTRACT

Aqueous, topical compositions contain an allylamine or an azole as an antifungal agent together with a lactate ester, an organic acid (pKa 3.8-5), ethanol, water, and a cationic galactomannan gum.

16 Claims, 10 Drawing Sheets

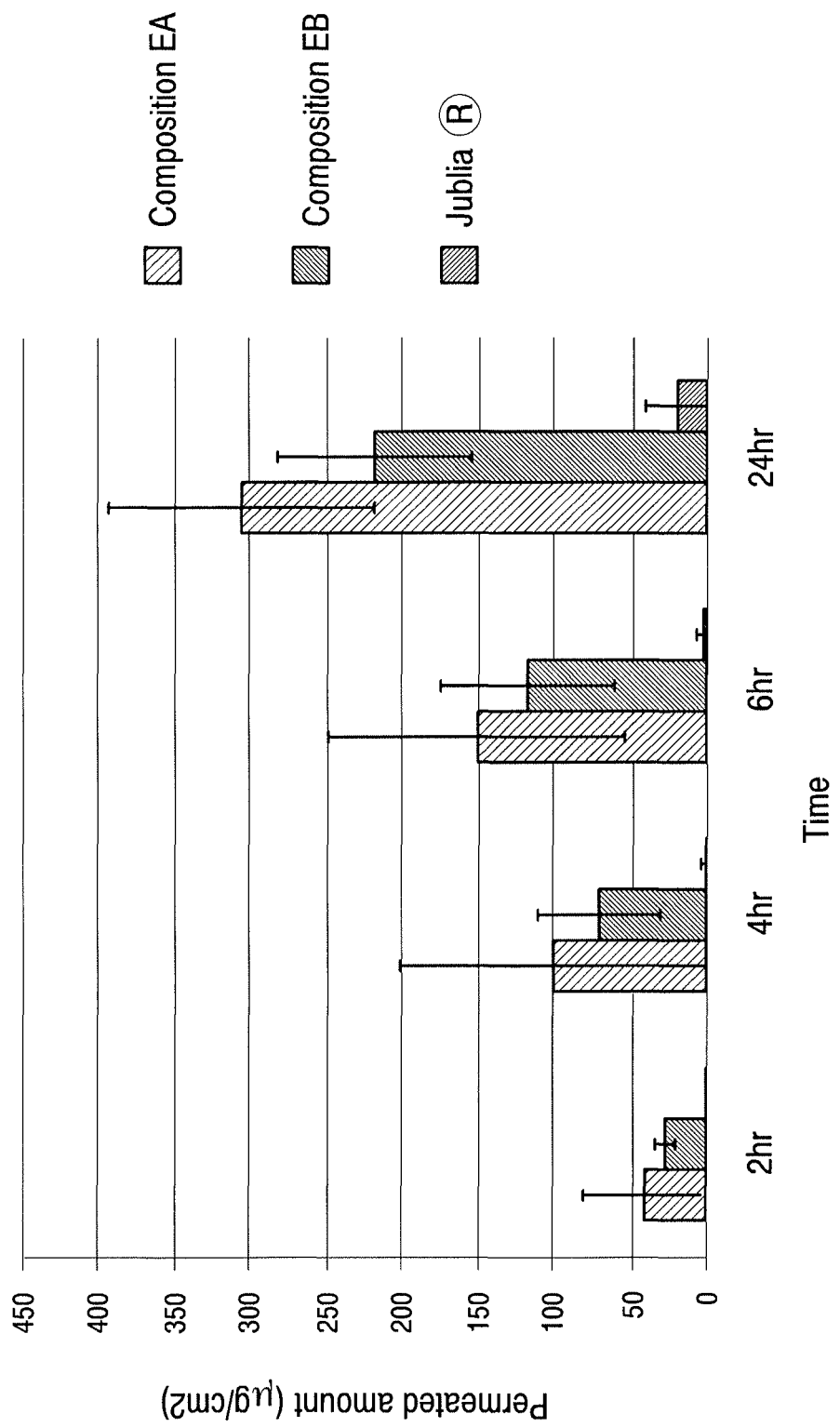

TOPICAL ANTIFUNGAL COMPOSITIONS

CROSS-REFERENCE TO RELATED APPLICATIONS

This application is a continuation-in-part of U.S. patent application Ser. No. 15/760,390, filed on Mar. 15, 2018, which application is a 371 National Stage entry of PCT/US2016/055978, filed on Oct. 7, 2016, and claims benefit of U.S. Provisional Application No. 62/238,464, filed on Oct. 7, 2015, all incorporated herein by reference in their entireties.

FIELD OF INVENTION

This invention relates to topical antifungal compositions. More particularly, this invention relates to topical antifungal compositions having enhanced antifungal activity.

BACKGROUND OF THE INVENTION

Infections of skin, nails, hair, or mucous membranes by fungi are common.

Onychomycosis, in particular, is a frequent fungal infection of nails, involving up to about 15% of adult individuals between the ages of about 40 to about 60 years. Delivery of antifungal agents through the nail and into the nail beds as well as the surrounding skin has been difficult to date, and minimally effective.

SUMMARY OF INVENTION

A topical antifungal composition is provided. The antifungal agent is an allylamine or an azole. Also present in the topical composition are lactate esters of a $C_2$ to $C_{16}$ saturated aliphatic alcohol, an organic acid having a pKa value in the range of about 3.8 to about 5, ethanol, water, and a cationic galactomannan gum, preferably a cationic polygalactomannan gum ether salt.

A preferred allylamine antifungal agent is terbinafine hydrochloride. A preferred azole antifungal agent is efinaconazole. A preferred lactate ester is lauryl lactate. A preferred organic acid is acetic acid or lactic acid.

BRIEF DESCRIPTION OF DRAWINGS

In the drawings,

FIG. 10 shows cadaver skin permeation profiles for present antifungal efinaconazole compositions as well as that of a commercially available efinaconazole containing cream (10%) (Jublia® cream).

DESCRIPTION OF PREFERRED EMBODIMENTS

Figure 1:
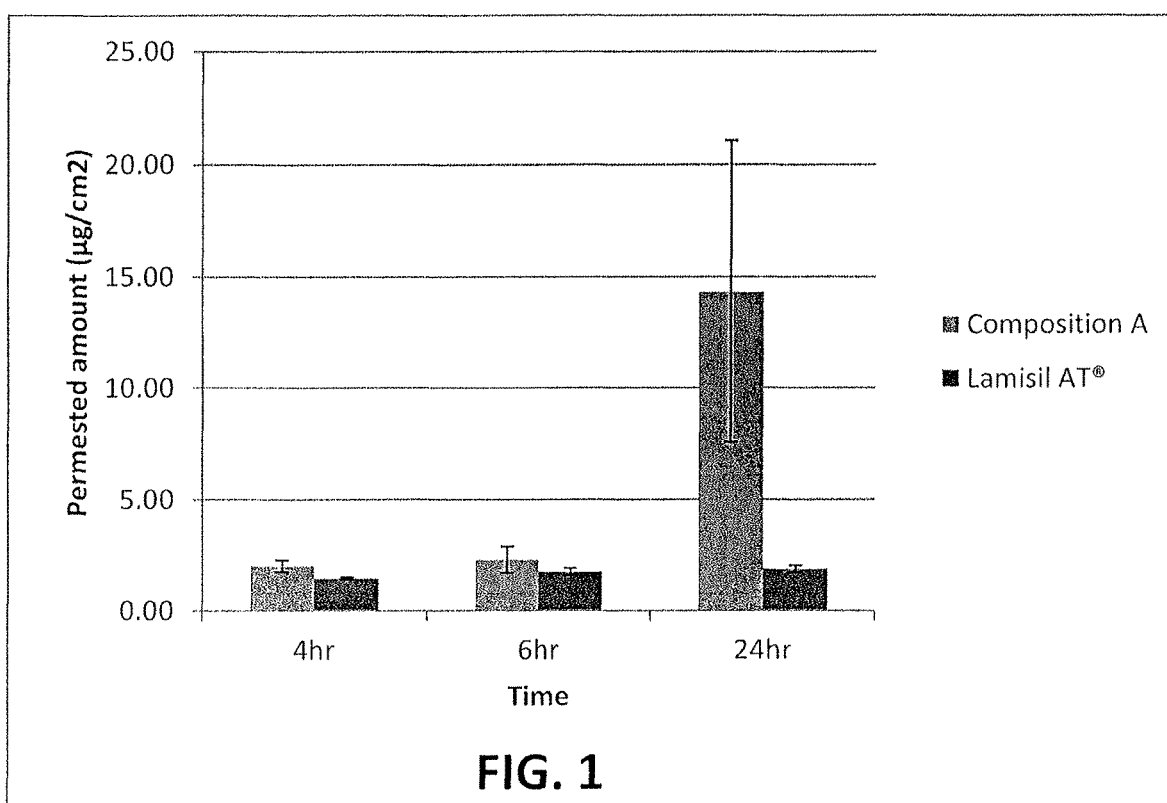
FIG. 1 shows shed snake skin permeation profiles of an aqueous terbinafine gel containing terbinafine hydrochloride, lauryl lactate, lactic acid, ethyl alcohol, water and hydroxypropyl guar hydroxypropyl trimonium chloride, as well as that of a commercially available terbinafine hydrochloride cream (1%) (Lamisil AT® Antifungal Cream)

The present aqueous topical compositions have the consistency of a gel, i.e., a substantially homogeneous semi-solid preparation having a liquid phase within a three dimensional polymeric matrix.

Suitable allylamine antifungal agents for the present compositions are terbinafine, naftifine, the allylamine-like compounds butenafine, amorolfine, as well as pharmaceutically acceptable salts of the foregoing. A preferred allylamine antifungal agent is terbinafine hydrochloride.

Allylamines inhibit ergosterol synthesis by fungi by the inhibition of squalene epoxidase, an enzyme involved in the fungal cell membrane synthesis pathway that prevents conversion of squalene to lanosterol, thereby inducing fungal cell lysis. In the present topical compositions, the allylamine is present in an amount in the range of about 0.5 to about 3 percent by weight, preferably about 1.2 percent by weight, based on the total weight of the composition.

Suitable azole antifungal agents for the present compositions are the imidazoles, the triazoles, and the thiazoles. Azole antifungal agents have similar activity against fungi as the allylamines, i.e., inhibition of the need to convert lanosterol to ergosterol. In the present topical compositions, the azole is present in an amount in the range of about 0.1 to about 5 percent by weight, preferably about 2 percent by weight, based on the total weight of the composition.

Illustrative imidazoles are ketoconazole, miconazole, isoconazole, clotrimazole, and the like.

Illustrative triazoles are efinaconazole, fluconazole, intraconazole, terconazole, and the like.

Illustrative thiazoles are abafungin, ethaboxam, thiabendazole, thiafluzamide, and the like.

Suitable lactate esters are the reaction products of lactic acid with a $C_2$ to $C_{16}$ saturated aliphatic alcohol. Illustrative such lactate esters are ethyl lactate, propyl lactate, n-butyl lactate, isoamyl lactate, 2-ethylhexyl lactate, lauryl lactate, cetyl lactate, and the like.

Lauryl lactate ($C_{15}H_{30}O_3$), the ester of lauryl alcohol and lactic acid, is a preferred lactate ester and is represented by the formula:

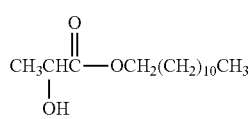

The lactate ester is present in the topical antifungal compositions in an amount in the range of about 1 to about 5 percent by weight, preferably about 3.5 percent by weight, based on the total weight of the composition.

Suitable organic acids for incorporation into the topical antifungal compositions can be monoprotic or polyprotic and have a pKa value in the range of about 3.8 to about 5. Illustrative monoprotic organic acids are glycolic acid (pKa 3.8), lactic acid (pKa 3.9), hydroxymethylbutyric acid (pKa 4.55), levulinic acid (pKa 4.6), acetic acid (pKa 4.8), caproic (hexanoic) acid (pKa 4.88), and the like. Illustrative diprotic acids are methyl succinic acid (pKa 4.13 and 5.64), succinic acid (pKa 4.21 and 5.64), glutaric acid (pKa 4.32 and 5.42) and the like. Monoprotic organic acids such as acetic acid and lactic acid are preferred.

The organic acid content of the present compositions is in the range of about 0.5 to about 5, preferably about 1 to about 4, percent by weight, based on the total weight of the composition.

The amount of ethanol present in the composition can be in the range of about 35 to about 55 percent, preferably about 40 to about 50 percent, by weight of the composition. The preferred organic acid-to-ethanol ratio is in the range of about 0.04 to about 0.09

The amount of water, preferably deionized water, can be present in the composition in the range of about 35 to about 55 percent, preferably about 40 to about 50 percent, by weight of the composition. The preferred water-to-ethanol weight ratio is in the range of about 1 to 1.1.

Another constituent of the topical antifungal compositions is a galactomannan gum derivatized with a cationic substituent. Nonionic substituents can be present as well.

The term "degree of substitution" or "DS" is used herein to indicate the average number of cationic-substituted hydroxyl groups relative to the total number of available hydroxyl groups per monomeric sugar unit in the guar polymer or gum. The monomeric sugar units of guar gum have on the average three (3) hydroxyl groups available for functionalization. Thus the value of DS is necessarily in the range of 0 to 3. A DS value of 0.10 corresponds to ten (10) cationic groups per every 100 sugar units.

For cationic galactomannan gums such as cationic guar gum the degree of substitution or DS preferably has a value in the range of about 0.07 to about 0.2.

The term "molar substitution" or "MS" is used herein to indicate the number of nonionic-substituted hydroxyl groups relative to the total number of available hydroxyl groups per monomeric sugar unit in the guar polymer or gum. Typical nonionic substituents are the hydroxyalkyl groups such as the hydroxyethyl and hydroxypropyl groups. For cationic galactomannan gums such as cationic guar gum the molar substitution or MS preferably has a value in the range of about 0.4 to 0.8.

Illustrative are guar hydroxypropyl trimonium chloride, hydroxypropyl guar trimonium chloride, and the like. Preferred are salts of a cationic polygalactomannan gum ether. This particular constituent has been found to provide an unexpected but desirable enhancement in the skin permeation of the active antifungal agent in the presence of the lactate ester and the monoprotic organic acid. Particularly preferred is hydroxypropyl guar hydroxypropyl trimonium chloride. Other quaternary ammonium derivatives of gums can be used as well for this purpose.

The cationic galactomannan gum can be present in an amount in the range of about 1 to about 3 percent by weight (dry basis), preferably about 2 to about 2.5 percent by weight (dry basis), based on the total weight of the composition.

The topical antifungal compositions can be prepared in the following manner:

The cationic galactomannan gum, such as hydroxypropyl guar hydroxypropyl trimonium chloride, is thoroughly dispersed in water. In a separate vessel the antifungal agent is combined with the lactate ester and the other remaining ingredients, and the resulting mixture is dissolved in ethanol. After the added organic acid has been dissolved, an aliquot of water is added with thorough mixing.

The obtained water-ethanol solution is then combined with the cationic galactomannan gum dispersion with vigorous agitation for a time period of at least about two hours until a substantially homogeneous gel is achieved. Thereafter any entrained air bubbles are removed. Preferably, the obtained gel is left standing before packaging for a time period sufficient for any entrained air bubbles to disperse.

An illustrative topical antifungal composition embodying the invention is set forth in Table I below.

TABLE 1

Topical Antifungal Composition
(Composition A)

| Ingredient | Amount, wt.-% |
| --- | --- |
| Terbinafine HCl | 1.2 |
| Lauryl lactate[1] | 3.5 |
| Lactic acid | 2.4 |
| Water, deionized | 47.1 |
| Ethyl alcohol USP (200 proof) | 43.4 |
| Hydroxypropyl guar hydroxypropyl trimonium chloride[2] | 2.4 |
| Water/Ethanol | 1.085 |
| Lactic acid/Ethanol | 0.055 |
| TOTAL | 100 |

[1]Schercemol LL ester

[2]Jaguar C162; CAS No. 71329-50-5; DS 0.10; MS 0.6; contains 11.5% w/w water (Solvay USA Inc., Cranbury, NJ 08512-7500)

A skin permeation study was performed with the composition shown in Table 1 using shed snake skin in a Franz cell (3.65 ml volume, 0.55 cm$^2$ surface area) with heating/stirring blocks and at a temperature of 35° C. Receptor compartment contained saline with sodium azide (pH 5.5). Three or four replicates (25 μl and a 25 mg control) were prepared. Sampling volume was 300 μl. Fresh buffer was replaced after each sample removal. Sampling was carried out at 4, 6 and 24 hours. The obtained samples were assayed using high performance liquid chromatography (HPLC). The control was a terbinafine containing cream (1%) commercially available under the designation Lamisil AT® antifungal cream.

The obtained permeation profile for the composition in Table 1, above, is presented in FIG. 1 and in Table 2, below.

TABLE 2

Permeation Data

| | Cumulative Amount in Receptor, μg/cm² | | | |
|---|---|---|---|---|
| Time, Hrs. | Composition A | ±SD | Control | ±SD |
| 4 | 2.05 | 0.26 | 1.48 | 0.06 |
| 6 | 2.32 | 0.81 | 1.79 | 0.15 |
| 24 | 14.30 | 7.07 | 1.91 | 0.15 |

The foregoing data show enhanced permeation of terbinafine hydrochloride as compared to the commercially available composition which contains approximately the same amount of terbinafine.

Permeation of Composition A through cadaver nails was studied in Franz cells, as described hereinabove, using a set of the cadaver nails from a 52-year old male as the Franz cell membrane. Cadaver nails were obtained from Science Care, Phoenix, Ariz.

The nail thickness was measured to be 0.65 to 1 millimeter.

Phosphate buffered saline (PBS, pH 5.5) was used as the receptor phase during each study.

Composition A was applied daily to each nail during the course of each study.

A one-week time period between successive studies was maintained. During this one-week time period the Franz cells were kept at 32° C. with stirring but no application of Composition A or sampling was taking place.

At the beginning of the next study, the receptor phase was removed, the receptor was rinsed with PBS at pH 5.5, and fresh PBS at pH 5.5 was introduced into the receptor compartment.

The control was a terbinafine-containing cream (1%) commercially available under the designation Lamisil AT® antifungal cream.

Figure 2:
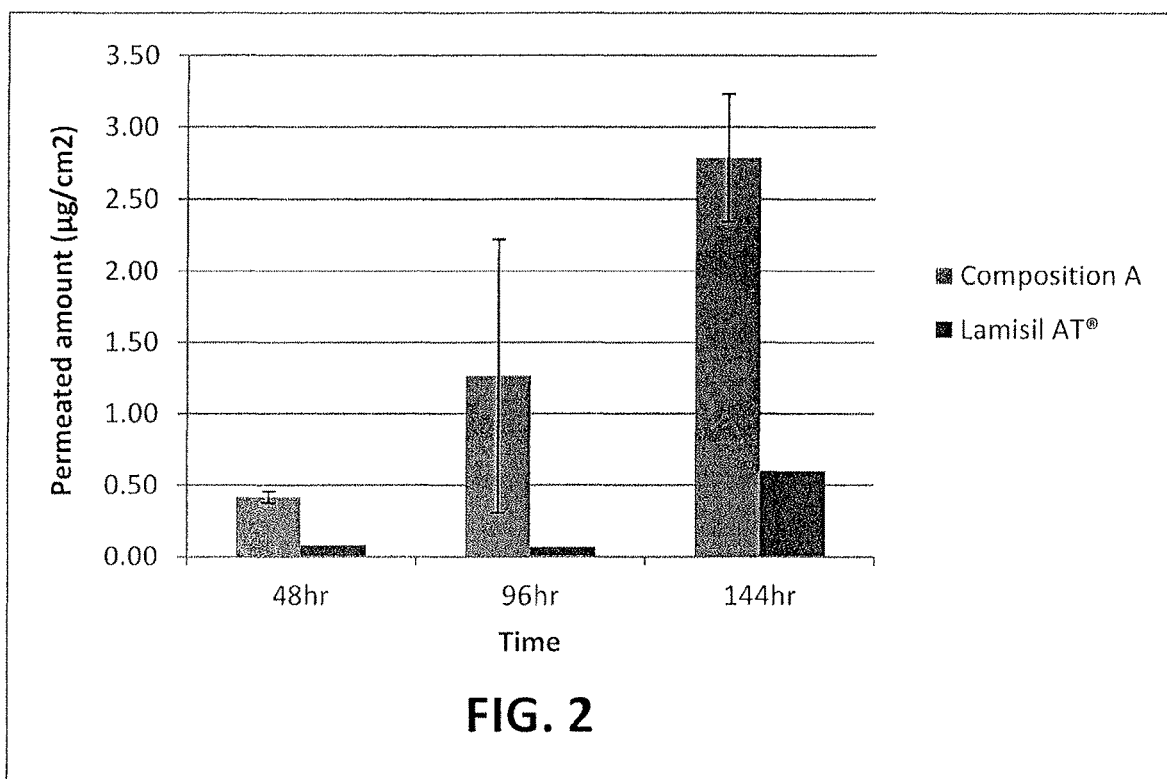
FIG. 2 shows the permeation profiles through a male cadaver nail of the same compositions as in FIG. 1.
Figure 3:
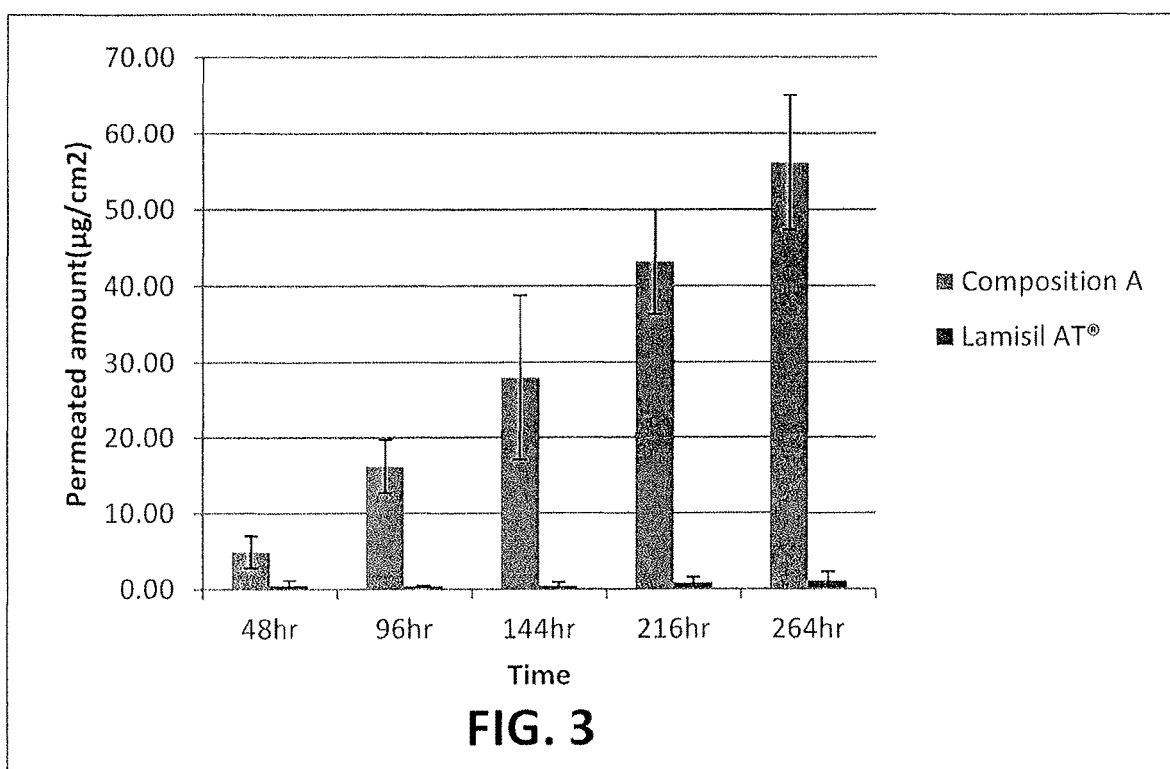
FIG. 3 shows the permeation profiles through the same male cadaver nail of the same compositions as in FIG. 1 measured one week after the permeation profiles shown in FIG. 2 were obtained.
Figure 4:
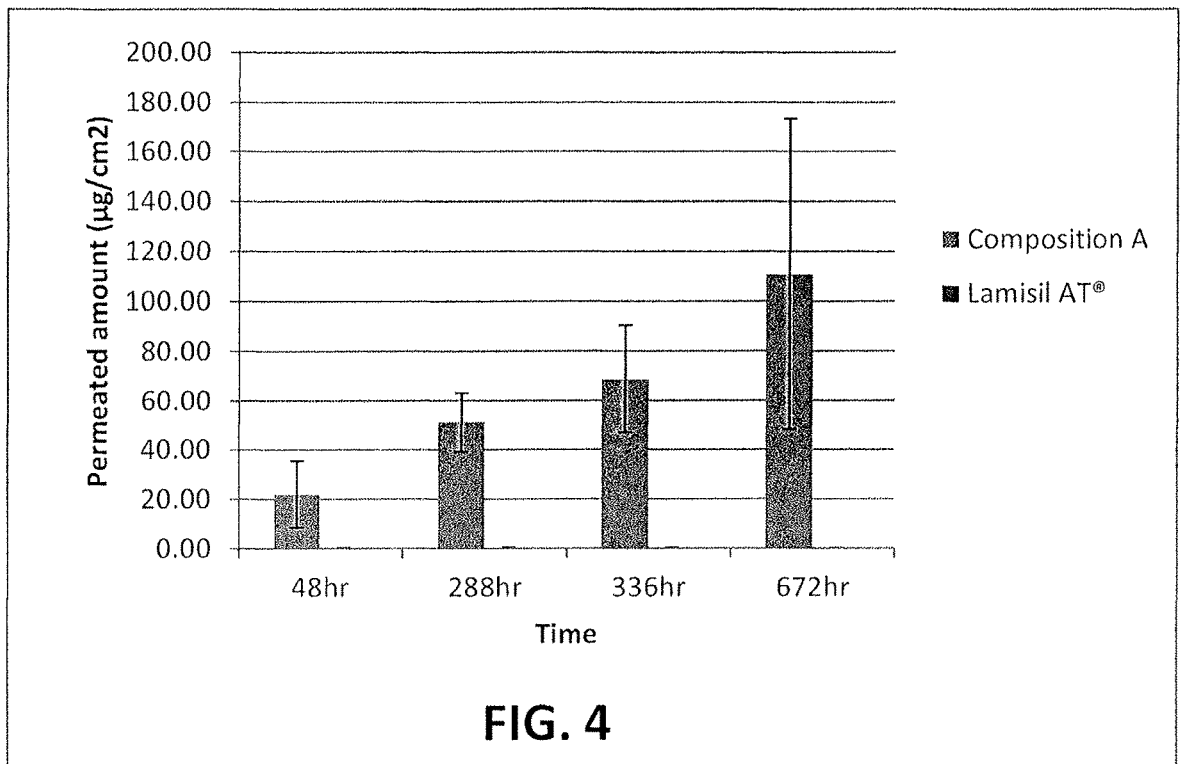
FIG. 4 shows the permeation profiles through the same male cadaver nail of the same compositions as in FIG. 1 measured one week after the permeation profiles shown in FIG. 3 were obtained.

The results of three consecutive studies using the same cadaver nail set are presented in FIGS. 2, 3 and 4 and in Tables 3, 4 and 5 below.

TABLE 3

Nail Permeation Data (Study 1)

| | Cumulative Amount in Receptor, μg/cm² | | | |
|---|---|---|---|---|
| Time, Hrs. | Composition A | ±SD | Control | ±SD |
| 48 | 0.42 | 0.04 | 0.08 | 0 |
| 96 | 1.27 | 0.96 | 0.07 | 0 |
| 144 | 2.79 | 0.44 | 0.06 | 0 |

TABLE 4

Nail Permeation Data (Study 2)

| | Cumulative Amount in Receptor, μg/cm² | | | |
|---|---|---|---|---|
| Time, Hrs. | Composition A | ±SD | Control | ±SD |
| 48 | 4.88 | 2.11 | 0.47 | 0.67 |
| 96 | 16.17 | 3.54 | 0.39 | 0.03 |
| 144 | 27.94 | 10.87 | 0.41 | 0.47 |
| 216 | 43.14 | 6.84 | 0.83 | 0.69 |
| 264 | 56.19 | 8.84 | 1.07 | 1.19 |

TABLE 5

Nail Permeation Data (Study 3)

| | Cumulative Amount in Receptor, μg/cm² | | | |
|---|---|---|---|---|
| Time, Hrs. | Composition A | ±SD | Control | ±SD |
| 48 | 22.04 | 13.41 | 0.15 | 0.07 |
| 288 | 51.14 | 12.04 | 0.25 | 0.15 |
| 336 | 68.52 | 21.79 | 0.20 | 0.16 |
| 672 | 110.79 | 62.60 | 0.25 | 0.01 |

The foregoing nail permeation data show that the composition embodying the present invention provides significantly enhanced terbinafine permeation through the human nail as compared to a commercially available topical terbinafine cream. In addition the foregoing data show that terbinafine from the present topical compositions accumulates or is retained in the nail.

After the completion of the aforedescribed nail permeation studies, the nails were removed from the Franz cells, wiped dry with lint free paper tissues (Kim-Wipes™) further cleaned twice with Qtips® cotton swabs soaked in absolute ethanol, and then dried at room temperature.

The dried nails then were cut into pieces (2 mm×2 mm) with stainless steel scissors, transferred into capped vials and extracted with ethanol (about 2 ml/vial) overnight at 37° C. with agitation. The obtained extracts were centrifuged and the obtained supernatant liquid analyzed by HPLC.

Figure 5:
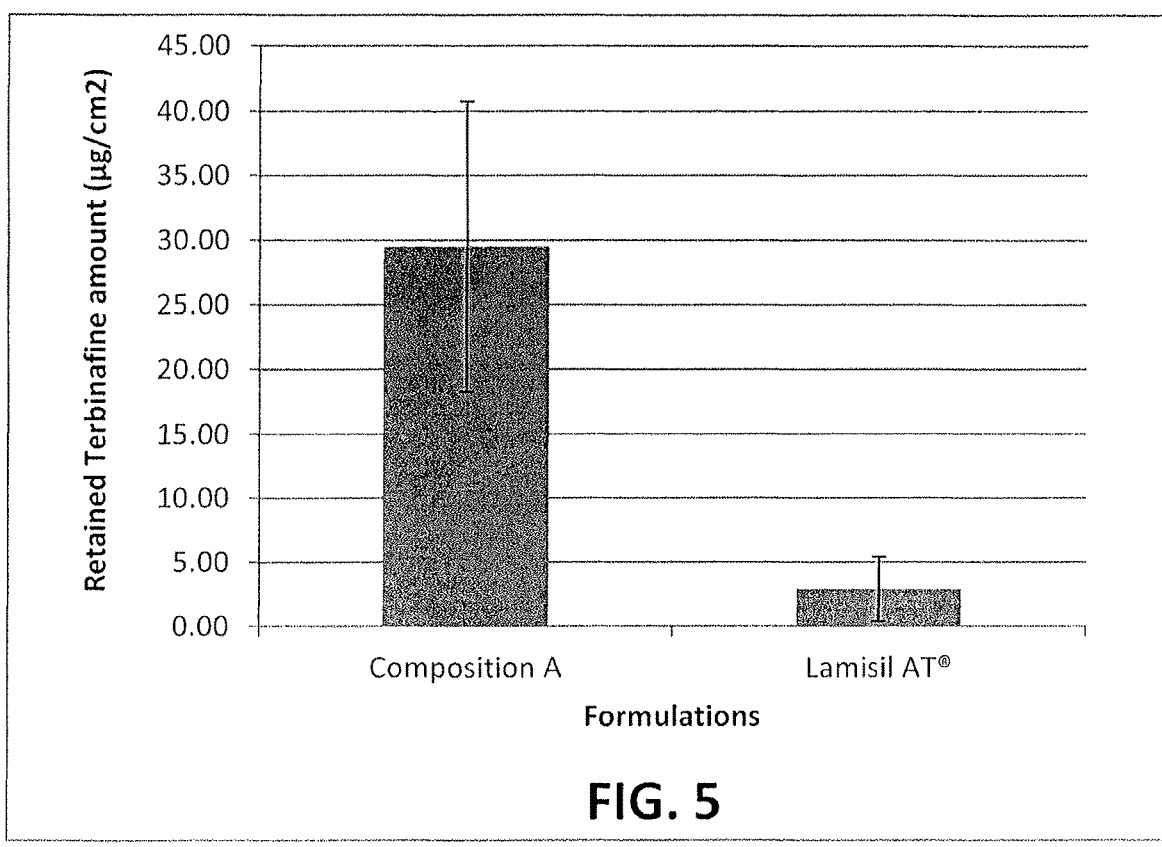
FIG. 5 shows terbinafine hydrochloride retention profile after two consecutive male cadaver nail permeation studies performed one week apart.

The obtained terbinafine retention profile is shown in FIG. 5 and presented in Table 6, below.

TABLE 6

Nail Retention Profile

| Composition | Average Amount Retained, μg/cm² | ±SD |
|---|---|---|
| Composition A | 29.51 | 11.23 |
| Control | 2.88 | 2.5 |

The above data show that a considerably larger amount of Composition A was retained in the nail as compared to the control, Lamisil AT® antifungal cream.

The permeability profiles of terbinafine topical antifungal compositions containing various organic acids with different dissociation constants (pKa values) were investigated. The compositions are set forth in Table 7, below. The permeation profiles of these compositions were determined in Franz cells using shed snake skin membranes.

TABLE 7

Terbinafine Antifungal Compositions

| Ingredient/wt.-% | A | B | C | D | E | F | G | H | I | J[2] | Lamisil AT® |
|---|---|---|---|---|---|---|---|---|---|---|---|
| Terbinafine HCl | 1.2 | 1.2 | 1.2 | 1.2 | 1.2 | 1.2 | 1.2 | 1.2 | 1.2 | 1.2 | 1 |
| Lauryl lactate | 3.5 | 3.5 | 3.5 | 3.5 | 3.5 | 3.5 | 3.5 | 3.5 | 3.5 | 3.5 | |
| Water, deionized | 47.1 | 47.1 | 47.1 | 47.1 | 47.1 | 47.1 | 47.1 | 47.1 | 47.1 | 45.8 | |
| Ethyl alcohol USP (200 Proof) | 43.4 | 43.4 | 43.4 | 43.4 | 43.4 | 43.4 | 43.4 | 43.4 | 44.6 | 43.5 | |
| Jaguar C162[1] | 2.4 | 2.4 | 2.4 | 2.4 | 2.4 | 2.4 | 2.4 | 2.4 | 1.2 | 3.6 | |
| Lactic acid (pKa 3.9) | 2.4 | | | | | | | | 2.4 | 2.4 | |
| Levulinic acid (pKa 4.6) | | 2.4 | | | | | | | | | |
| Hydroxymethylbutyric acid (pKa 4.55) | | | 2.4 | | | | | | | | |
| Citric acid (pKa 3.09; 4.75; 5.41) | | | | 2.4 | | | | | | | |
| Acetic acid (pKa 4.8) | | | | | 2.4 | | | | | | |
| Maleic acid (pKa 1.93; 6.58) | | | | | | 2.4 | | | | | |
| Malic acid (pKa 3.40; 5.2) | | | | | | | 2.4 | | | | |
| Caproic acid (pKa 4.88) | | | | | | | | 2.4 | | | |
| TOTAL | 100 | 100 | 100 | 100 | 100 | 100 | 100 | 100 | 100 | 100 | |

Figure 6:
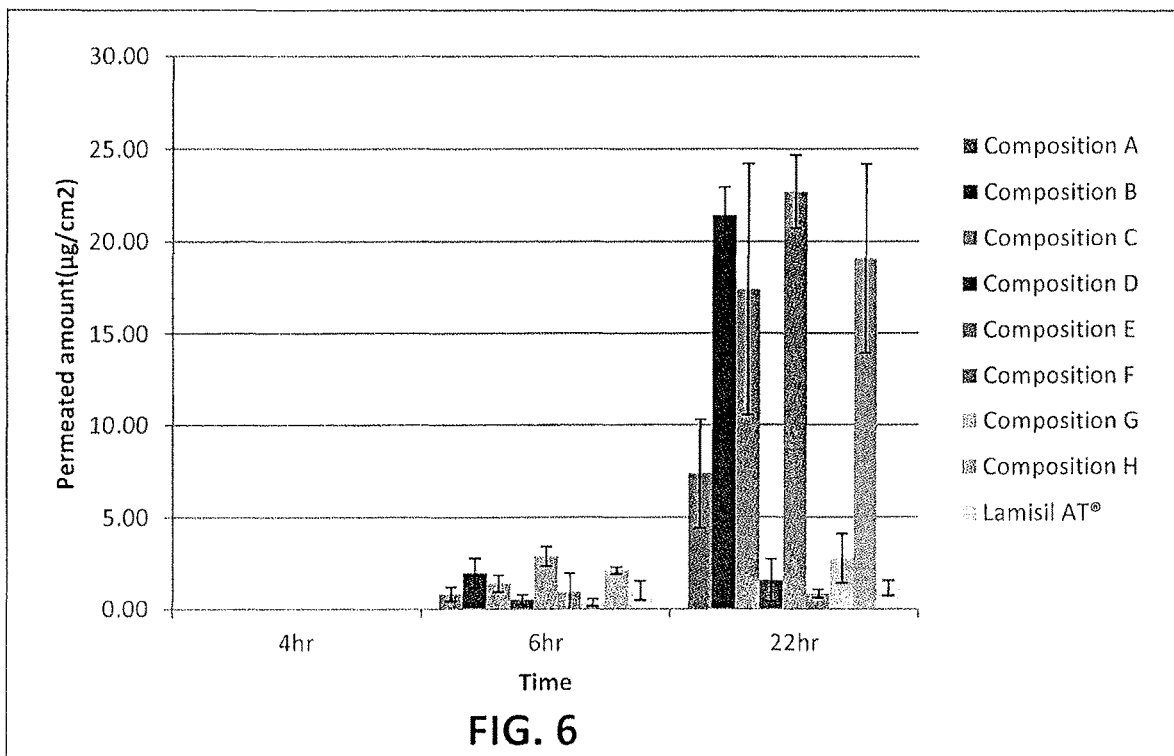
FIG. 6 shows terbinafine hydrochloride shed snake skin permeation profiles in topical compositions containing monoprotic and polyprotic organic acids having different pKa values.

[1]Hydroxypropyl guar hydroxypropyl trimonium chloride; CAS No. 71329-50-5; contains 11.5% w/w water
[2]Composition J exhibited unacceptably high viscosity The obtained permeation profiles are shown in FIG. 6, and are presented in Table 8, below.

TABLE 8

Permeation Profiles of Compositions A-I

Cumulative Amount ($\mu g/cm^2$) per Composition

| Time, Hrs. | A ± SD | B ± SD | C ± SD | D ± SD | E ± SD | F ± SD | G ± SD | H ± SD | I ± SD | Lamisil AT® |
|---|---|---|---|---|---|---|---|---|---|---|
| 2 | 0.00 ± 0.00 | 0.00 ± 0.00 | 0.00 ± 0.00 | 0.00 ± 0.00 | 0.00 ± 0.00 | 0.00 ± 0.00 | 0.00 ± 0.00 | 0.00 ± 0.00 | 0.00 ± 0.00 | 0.00 |
| 4 | 0.00 ± 0.00 | 0.00 ± 0.00 | 0.00 ± 0.00 | 0.00 ± 0.00 | 0.00 ± 0.00 | 0.00 ± 0.00 | 0.00 ± 0.00 | 0.00 ± 0.00 | 0.00 ± 0.00 | 0.00 |
| 6 | 0.83 ± 0.38 | 1.98 ± 0.81 | 1.41 ± 0.46 | 0.53 ± 0.26 | 2.88 ± 0.52 | 0.93 ± 1.04 | 0.35 ± 0.20 | 2.11 ± 0.17 | 1.92 ± 1.98 | 1.01 |
| 22 | 7.36 ± 2.94 | 21.43 ± 1.51 | 17.38 ± 6.83 | 1.58 ± 1.14 | 22.69 ± 1.98 | 0.85 ± 0.22 | 2.77 ± 1.33 | 19.07 ± 5.13 | 7.60 ± 6.93 | 1.15 |

The above data show that all but Composition F exhibited enhanced permeation as compared to commercial product Lamisil AT® antifungal cream, and that Compositions A, B, C, E, H and I, containing a monoprotic organic acid with a pKa value in the range of about 3.8 to about 5 exhibited substantially enhanced permeation.

Stability of Composition A samples was evaluated by storage at 25° C. and 40° C. for extended time periods in phenolic capped glass vials. Thereafter aliquots of the stored samples were analyzed by high performance liquid chromatography (HPLC). The observed results are shown in Table 9, below.

TABLE 9

Stability of Terbinafine Hydrohchloride Containing Composition A

| Terbinafine HCl, wt.-% | Temperature, ° C. | Storage Time, months | Amount Recovered, wt.-% | ±SD |
|---|---|---|---|---|
| 1.2 | 25 | 2 | 109.19 | 2.24 |
| 1.2 | 25 | 4 | 108.04 | 3.30 |
| 1.2 | 25 | 7 | 107.97 | 0.66 |
| 1.2 | 40 | 1 | 112.6 | 1.39 |
| 1.2 | 40 | 3 | 110.33 | 1.16 |
| 1.2 | 40 | 6 | 110.07 | 0.38 |

HPLC chromatograms of aliquots taken from the stored samples did not reveal any peaks due to decomposition. Similar permeation profiles were observed for samples stored for four months at 25° C. and at 40° C.

The slightly higher observed values for amounts recovered are believed to be due to some loss of ethyl alcohol due to the containers used to store the samples.

Further illustrative topical antifungal compositions embodying the invention are set forth in Table 10, below.

TABLE 10

Topical Antifungal Compositions
(Compositions K and L)

| Ingredient | Amount wt.-% | |
|---|---|---|
| | K | L |
| Amorolfine HCl | 1.2 | 2.4 |
| Lauryl lactate[1] | 3.5 | 3.5 |
| Lactic acid | 2.4 | 2.4 |
| Water, deionized | 47.1 | 45.8 |
| Ethyl alcohol USP, absolute | 43.4 | 43.5 |
| Hydroxypropyl guar hydroxypropyl trimonium chloride[2] | 2.4 | 2.4 |
| Water/Ethanol | 1.085 | 1.053 |
| Lactic acid/Ethanol | 0.056 | 0.55 |
| TOTAL | 100 | 100 |

[1]Schercemol LL ester
[2]Jaguar C162; CAS No. 71329-50-5; DS 0.10; MS 0.6; contains 11.5% w/w water A skin permeation study was performed using the compositions shown in Table 10, above. Shed snake skin was used in a Franz cell (3.65 ml volume, 0.55 cm$^2$ surface area) with heating/stirring blocks and at a temperature of 35° C. Receptor compartment contained saline with sodium azide (pH 5.5). Three or four replicates (25 µl and a 25 mg control) were prepared. Sampling volume was 300 µL. Fresh buffer was replaced after each sample removal. Sampling was carried out at 2, 4, 6 and 24 hours. The obtained samples were assayed using high performance liquid chromatography (HPLC). The control was a commercially available, amorolfine containing cream (5%), Loceryl® cream, Galderma Laboratorium, Germany, having the following composition:
  amorolfine HCl (5%)
  ammonio methacrylate polymer
  triacetin
  butyl acetate
  ethyl acetate
  ethanol (61%).

Figure 7:
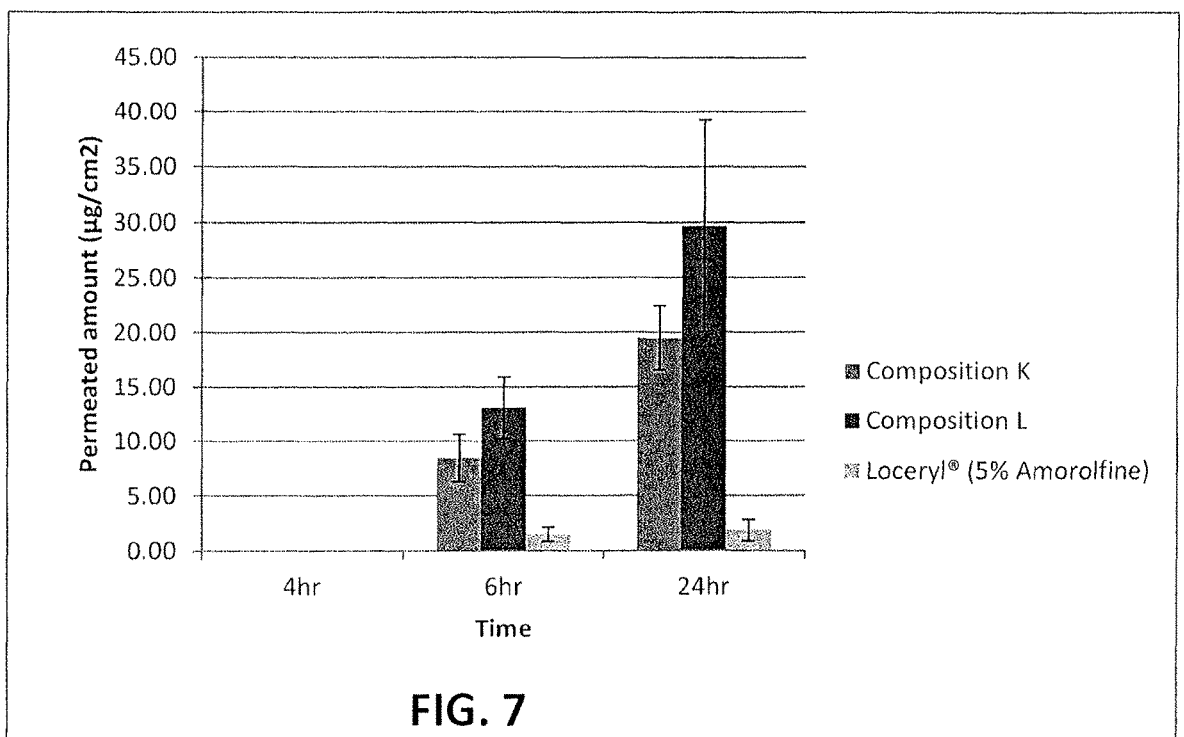
FIG. 7 shows shed snake skin permeation profiles of an aqueous amorolfine gel containing amorolfine hydrochloride, lauryl lactate, lactic acid, ethyl alcohol, water, and hydroxypropyl guar hydroxypropyltrimonium chloride as well as that of a commercially available amorolfine hydrochloride preparation, Loceryl® (5%) cream.

The obtained permeation profiles for the compositions in Table 10 are presented in FIG. 7 and Table 11, below.

TABLE 11

Permeation Data

| Time, Hrs. | Cumulative Amount in Receptor, µg/cm$^2$ | | | | | |
|---|---|---|---|---|---|---|
| | Composition K | ±SD | Composition L | ±SD | Loceryl ® | ±SD |
| 2 | 0 | 0 | 0 | 0 | 0 | 0 |
| 4 | 0 | 0 | 0 | 0 | 0 | 0 |
| 6 | 8.46 | 2.17 | 13.05 | 2.85 | 1.49 | 0.64 |
| 24 | 19.49 | 2.94 | 29.66 | 9.63 | 1.87 | 0.96 |

The foregoing data show enhanced permeation of amorolfine hydrochloride as compared to commercially available preparations containing the same active ingredient albeit at a relatively higher concentration.

Figure 8:
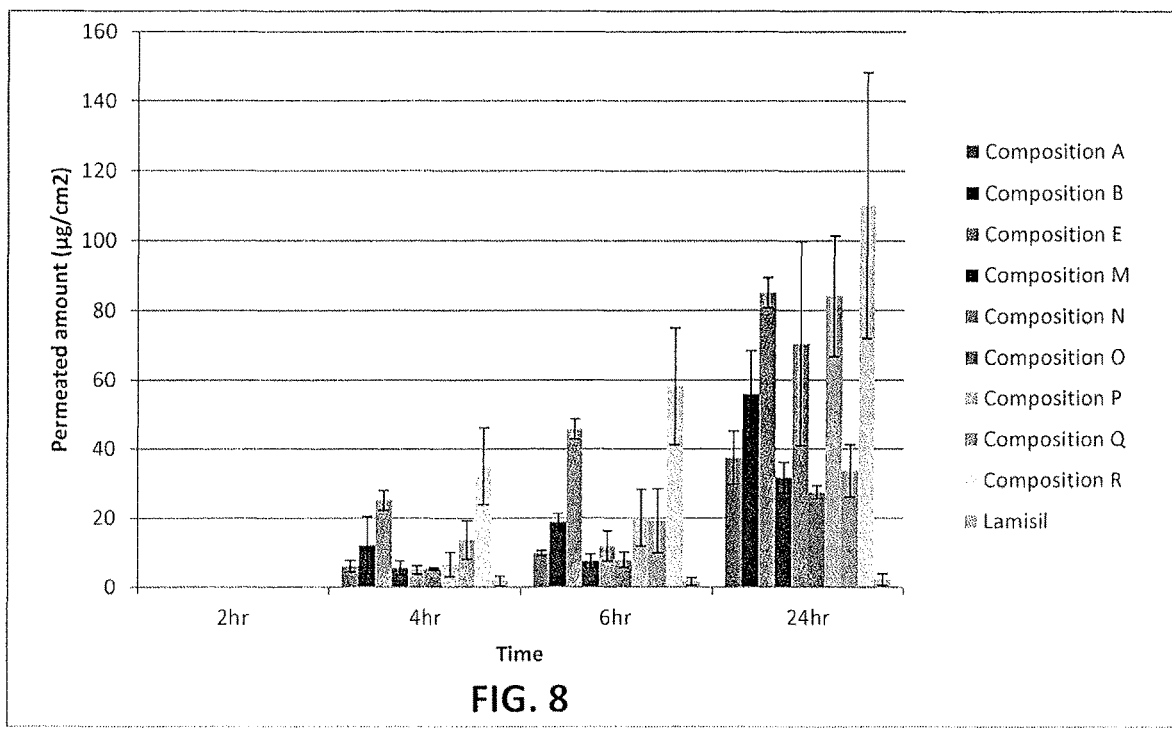
FIG. 8 shows shed snake skin permeation profiles of an aqueous terbinafine gel with various lactic, levulinic and acetic acid levels.

The permeation profiles of terbinafine antifungal compositions through shed snake skin at varying concentrations of lactic acid, levulinic acid and acetic acid were evaluated. The evaluated compositions are shown in Table 12, below. The observed permeation profiles are presented in FIG. 8 and Table 13, below.

TABLE 12

Terbinafine Antifungal Compositions

| Ingredient/wt.-% | Composition | | | | | | | | | Lamisil AT ® |
|---|---|---|---|---|---|---|---|---|---|---|
| | A | M | N | B | O | P | E | Q | R | |
| Terbinafine HCl | 1.2 | 1.2 | 1.2 | 1.2 | 1.2 | 1.2 | 1.2 | 1.2 | 1.2 | 1 |
| Lauryl lactate | 3.5 | 3.5 | 3.5 | 3.5 | 3.5 | 3.5 | 3.5 | 3.5 | 3.5 | |
| Water, deionized | 47.1 | 47.1 | 45.8 | 47.1 | 47.1 | 45.8 | 47.1 | 47.1 | 45.8 | |
| Ethyl alcohol USP (200 Proof) | 43.4 | 44.6 | 43.5 | 43.4 | 44.6 | 43.5 | 43.4 | 44.6 | 43.5 | |
| Jaguar C162[1] | 2.4 | 2.4 | 2.4 | 2.4 | 2.4 | 2.4 | 2.4 | 2.4 | 2.4 | |
| Lactic acid (pKa 3.9) | 2.4 | 1.2 | 3.6 | | | | | | | |
| Levulinic acid (pKa 4.6) | | | | 2.4 | 1.2 | 3.6 | | | | |
| Acetic acid (pKa 4.8) | | | | | | | 2.4 | 1.2 | 3.6 | |
| TOTAL | 100 | 100 | 100 | 100 | 100 | 100 | 100 | 100 | 100 | |

[1]Hydroxypropyl guar hydroxypropyl trimonium chloride; CAS No. 71329-50-5; DS 0.10; MS 0.6; contains 11.5% w/w water

TABLE 13

Permeation Profiles of Compositions in Table 12

| Time, Hrs. | Cumulative Amount (µg/cm$^2$) per Composition | | | | | |
|---|---|---|---|---|---|---|
| | A ± SD | B ± SD | E ± SD | M ± SD | N ± SD | O ± SD |
| 2 | 0.00 ± 0.00 | 0.00 ± 0.00 | 0.00 ± 0.00 | 0.00 ± 0.00 | 0.00 ± 0.00 | 0.00 ± 0.00 |
| 4 | 6.06 ± 1.68 | 12.08 ± 8.33 | 25.02 ± 2.86 | 5.50 ± 1.99 | 5.00 ± 1.21 | 5.35 ± 0.31 |
| 6 | 9.82 ± 0.65 | 18.78 ± 2.44 | 45.67 ± 2.82 | 7.53 ± 1.99 | 11.87 ± 4.40 | 7.84 ± 2.20 |
| 24 | 37.4 ± 7.67 | 55.70 ± 12.55 | 85.04 ± 4.24 | 31.61 ± 4.45 | 70.34 ± 29.42 | 27.43 ± 1.86 |

TABLE 13-continued

Permeation Profiles of Compositions in Table 12

| Time, Hrs. | Cumulative Amount (µg/cm²) per Composition | | | |
|---|---|---|---|---|
| | P ± SD | Q ± SD | R ± SD | Lamisil AT ® |
| 2 | 0.00 ± 0.00 | 0.00 ± 0.00 | 0.00 ± 0.00 | 0.00 ± 0.00 |
| 4 | 6.51 ± 3.48 | 13.65 ± 5.57 | 34.91 ± 11.06 | 1.77 ± 1.47 |
| 6 | 20.06 ± 8.19 | 19.14 ± 0.29 | 58.08 ± 16.91 | 1.66 ± 1.12 |
| 24 | 84.06 ± 17.36 | 33.64 ± 7.52 | 110.14 ± 38.24 | 2.23 ± 1.59 |

The above data show that relatively higher acid content enhanced permeation, and that acetic acid containing compositions provided highest permeation.

Figure 9:
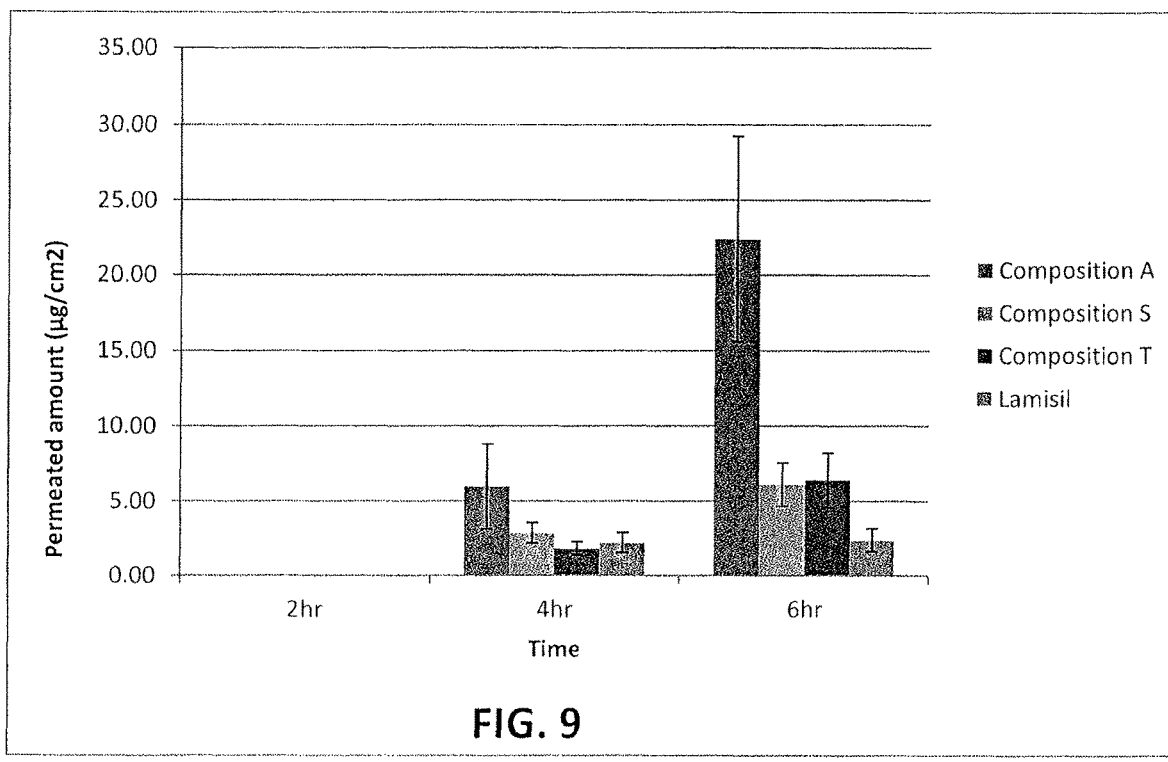
FIG. 9 shows shed snake skin permeation profiles of an aqueous terbinafine gel with cationic and nonionic guar gum thickeners.

The permeation profiles of terbinafine antifungal compositions through shed snake skin and utilizing various guar gums were evaluated as well. The evaluated compositions are shown in Table 14, below. The observed permeation profiles are presented in FIG. 9 and Table 15, below.

TABLE 14

Terbinafine Antifungal Compositions

| Ingredient/wt.-% | Composition | | | |
|---|---|---|---|---|
| | A | S | T | Lamisil AT ® |
| Terbinafine HCl | 1.2 | 1.2 | 1.2 | 1 |
| Lauryl lactate | 3.5 | 3.5 | 3.5 | |
| Lactic acid | 2.4 | 2.4 | 2.4 | |
| Water, deionized | 47.1 | 47.1 | 47.1 | |
| Ethyl alcohol USP (200 proof) | 43.4 | 43.4 | 43.4 | |
| Jaguar C162[1] | 2.4 | | | |
| Jaguar HP 105[2] | | 2.4 | | |
| Jaguar HP 120[3] | | | 2.4 | |
| TOTAL | 100 | 100 | 100 | |

[1]Hydroxypropyl guar hydroxypropyl trimonium chloride; CAS No. 71329-50-5; DS 0.10; MS 0.6; contains 11.5% w/w water

[2]Nonionic guar gum, 2-hydroxypropyl ether; CAS No. 39421; contains 6.4% w/w water; 0.6 MS

[3]Nonionic guar gum, 2-hydroxypropyl ether; CAS No. 39421-75-5; contains 7.5% w/w water; 1.2 MS

TABLE 15

Permeation Profiles of Compositions in Table 14

| Time, Hrs. | Cumulative Amount (µg/cm²) per Composition | | | |
|---|---|---|---|---|
| | A ± SD | S ± SD | T ± SD | Lamisil AT ® ± SD |
| 2 | 0.00 ± 0.00 | 0.00 ± 0.00 | 0.00 ± 0.00 | 0.00 ± 0.00 |
| 4 | 5.99 ± 2.83 | 2.88 ± 0.68 | 1.85 ± 0.45 | 2.23 ± 0.68 |
| 6 | 22.43 ± 6.82 | 6.10 ± 1.44 | 6.40 ± 1.83 | 2.39 ± 0.78 |

The above data show that a cationic guar gum provides a better permeation profile as compared to a nonionic guar gum.

The permeation behavior through shed snake skin of Composition A stored for a time period of six months at 25° C. and 40° C. was evaluated as well. The observed results are shown in Table 16, below.

TABLE 16

Permeation Profile of Composition A After Storage

| Time, Hrs. | Cumulative Amount (µg/cm²) per Composition | | |
|---|---|---|---|
| | A ± SD @ 25° C. | A ± SD @ 40° C. | Lamisil AT ® ± SD |
| 2 | 12.08 ± 2.39 | 21.76 ± 8.27 | 1.59 ± 0.17 |
| 6 | 31.07 ± 12.77 | 60.92 ± 19.75 | 1.44 ± 0.33 |
| 24 | 161.57 ± 52.44 | 204.40 ± 25.06 | 2.98 ± 0.88 |

Illustrative terbinafine antifungal compositions containing diprotic organic acids are shown in Table 17, below, and their permeation through shed shake skin is shown in Table 18, below.

TABLE 17

Terbinafine Antifungal Compositions With Diprotic Organic Acids

| Ingredient/wt.-% | Composition | | | |
|---|---|---|---|---|
| | A | U | V | Lamisil AT ® |
| Terbinafine HCl | 1.2 | 1.2 | 1.2 | 1 |
| Lauryl lactate | 3.5 | 3.5 | 3.5 | |
| Water, deionized | 47.1 | 47.1 | 47.1 | |
| Ethyl alcohol USP (200 proof) | 43.4 | 43.4 | 43.4 | |
| Jaguar C162[1] | 2.4 | 2.4 | 2.4 | |
| Lactic acid (pKa 3.9) | 2.4 | | | |
| Succinic acid (pKa 4.21; 5.64) | | 2.4 | | |
| Glutaric acid (pKa 4.32; 5.42) | | | 2.4 | |
| TOTAL | 100 | 100 | 100 | |

[1]Hydroxypropyl guar hydroxypropyl trimonium chloride; CAS No. 71329-50-5; DS 0.10; MS 0.6; contains 11.5% w/w water

TABLE 18

Permeation Profiles of Compositions A, U & V

| Time, Hrs. | Cumulative Amount (µg/cm²) per Composition | | | |
|---|---|---|---|---|
| | A ± SD | U ± SD | V ± SD | Lamisil AT ® ± SD |
| 4 | 12.08 ± 2.39 | 9.98 ± 2.23 | 9.49 ± 1.30 | 1.59 ± 0.17 |
| 6 | 31.07 ± 12.77 | 26.36 ± 7.96 | 29.15 ± 8.28 | 1.44 ± 0.33 |
| 24 | 161.57 ± 52.44 | 142.75 ± 38.24 | 163.22 ± 46.03 | 2.98 ± 0.88 |

Stability of Composition E and Composition R, both containing acetic acid, was evaluated after storage at 25° C. and 40° C. for a time period of one month and three months in phenolic capped glass vials. Aliquots of stored samples were analyzed by high performance liquid chromatography. The observed results are shown in Tables 19 and 20, below.

TABLE 19

Stability of Terbinafine Hydrochloride
Containing Composition E

| Terbinafine HCl, wt.-% | Temperature, °C. | Storage Time, months | Amount Recovered, wt.-% | ±SD |
|---|---|---|---|---|
| 1.2 | 25 | 0 | 104.53 | 1.53 |
| 1.2 | 25 | 1 | 105.30 | 1.06 |
| 1.2 | 25 | 3 | 102.15 | 2.33 |
| 1.2 | 40 | 0 | 104.53 | 1.53 |
| 1.2 | 40 | 1 | 105.02 | 0.95 |
| 1.2 | 40 | 3 | 103.82 | 2.11 |

TABLE 20

Stability of Terbinafine Hydrochloride
Containing Composition R

| Terbinafine HCl, wt.-% | Temperature, °C. | Storage Time, months | Amount Recovered, wt.-% | ±SD |
|---|---|---|---|---|
| 1.2 | 25 | 0 | 105.39 | 0.81 |
| 1.2 | 25 | 1 | 105.55 | 0.49 |
| 1.2 | 25 | 3 | 104.54 | 1.04 |
| 1.2 | 40 | 0 | 105.39 | 0.81 |
| 1.2 | 40 | 1 | 104.68 | 0.99 |
| 1.2 | 40 | 3 | 107.17 | 2.42 |

Data in the above Tables shows that the terbinafine hydrochloride compositions were stable after storage for three months at 25° C. and 40° C. in phenolic capped glass vials. The somewhat higher assays of recovered terbinafine hydrochloride are believed to be due to loss of ethanol by evaporation.

A preferred allylamine antifungal composition is a topical gel which includes terbinafine hydrochloride, lauryl lactate, water, ethanol, hydroxypropyl guar hydroxypropyl trimonium chloride and acetic acid.

A preferred water-to-ethanol weight ratio is in the range of about 1 to about 1.1.

A preferred acetic acid-to-ethanol weight ratio is in the range of about 0.04 to about 0.09.

A preferred amount of acetic acid for terbinafine hydrochloride topical gel compositions is in the range of about 2 to about 4 percent by weight, based on the total weight of the topical gel composition.

In a preferred topical gel composition terbinafine hydrochloride is present in an amount in the range of 0.5 to about 3 percent by weight, lauryl lactate is present in an amount in the range of about 1 to about 5 percent by weight, water, more preferably deionized water, is present in an amount in the range of about 35 to about 55 percent by weight, more preferably about 40 to about 50 percent by weight, ethanol is present in an amount in the range of about 35 to about 55 percent by weight, more preferably about 40 to about 50 percent by weight, and the hydroxypropyl guar hydroxypropyl trimonium chloride is present in an amount in the range of about 1.5 to about 3 percent by weight, more preferably about 2 to about 2.5 percent by weight. The aforesaid percentages by weight are based on the total weight of the topical gel composition.

The effect of water-ethanol weight ratio on terbinafine hydrochloride containing topical compositions is illustrated in Tables 21 and 22, below.

TABLE 21

Terbinafine HCl Compositions With Different Water/Ethanol Weight Ratios

| Ingredient, wt.-% | Composition | | | | | | | | |
|---|---|---|---|---|---|---|---|---|---|
| | R | AA | AB | AC | AD | AE | AF | AG | AH |
| Terbinafine HCl | 1.2 | 1.2 | 1.2 | 1.2 | 1.2 | 1.2 | 1.2 | 1.2 | 1.2 |
| Lauryl lactate[1] | 3.5 | 3.5 | 3.5 | 3.5 | 3.5 | 3.5 | 3.5 | 3.5 | 3.5 |
| Water, deionized | 45.8 | 49.3 | 54.3 | 59.3 | 64.3 | 69.3 | 39.3 | 34.3 | 29.3 |
| Ethanol USP (200 proof) | 43.5 | 40 | 35 | 30 | 25 | 20 | 50 | 55 | 60 |
| Hydroxypropyl guar hydroxypropyl trimonium chloride[2] | 2.4 | 2.4 | 2.4 | 2.4 | 2.4 | 2.4 | 2.4 | 2.4 | 2.4 |
| Acetic acid | 3.6 | 3.6 | 3.6 | 3.6 | 3.6 | 3.6 | 3.6 | 3.6 | 3.6 |
| Water/Ethanol | 1.053 | 1.233 | 1.551 | 1.977 | 2.572 | 3.465 | 0.786 | 0.624 | 0.488 |
| Acetic acid/Ethanol | 0.083 | 0.090 | 0.103 | 0.120 | 0.144 | 0.180 | 0.072 | 0.066 | 0.060 |
| TOTAL | 100.0 | 100.0 | 100.0 | 100.0 | 100.0 | 100.0 | 100.0 | 100.0 | 100.0 |

[1]Schercemol LL ester
[2]Jaguar C162; CAS No. 71329-50-5; DS 0.10; MS 0.6; contains 11/5% w/w water

TABLE 22

Terbinafine HCl Compositions Having Different Water/Ethanol Weight Ratios

| Time | Composition | | | | | | | | |
|---|---|---|---|---|---|---|---|---|---|
| | R | AA | AB | AC | AD | AE | AF | AG | AH |
| At 0 hr | clear gel | opaque gel | opaque gel | opaque gel | opaque gel | opaque gel | low viscosity gel | phase separation | gel separation |
| After 1 week | clear gel | opaque gel | opaque gel | phase separation | phase separation | phase separation | low viscosity gel | phase separation | gel separation |

The viscosity of prepared compositions R and AA through AH shown in Table 21, above, was measured using a Brookfield HBDV-I Prime viscometer using Spindle CPE-51. The viscometer was initialized, calibrated, and zeroed according to manufacturer's recommendations. About 1 gram of the topical composition was spread uniformly in the sample cup (CPE-44Y) of the viscometer and the motor speed was adjusted to 10 revolutions per minute. Viscosity in centipoises (CP) and percent torque were determined when readings stabilized. The results are shown in Table 23, below.

TABLE 23

Viscosity Results

| | Composition | | | | | | | |
|---|---|---|---|---|---|---|---|---|
| | R | AA | AB | AC | AD | AE | AF | AG | AH |
| Viscosity (cP) | 2361 | 2030.0 | 952.8 | n/a | n/a | n/a | 1988 | 456 | n/a |
| Torque (%) | 5.7 | 4.9 | 2.3 | n/a | n/a | n/a | 4.8 | 1.1 | n/a | n/a indicates unstable viscosity

Terbinafine hydrochloride compositions containing different amounts of cationic guar gum were investigated, the appearance thereof noted, and viscosity measured as described hereinabove. The prepared compositions, the noted appearance and measured viscosity are shown in Tables 24, 25 and 26, below.

TABLE 24

Terbinafine HCl Compositions With Different Amounts of Cationic Guar Gum

| | Composition | | | | | |
|---|---|---|---|---|---|---|
| Ingredient, wt.-% | R | AI | AJ | AK | AL | AM |
| Terbinafine HCl | 1.2 | 1.2 | 1.2 | 1.2 | 1.2 | 1.2 |
| Lauryl lactate[1] | 3.5 | 3.5 | 3.5 | 3.5 | 3.5 | 3.5 |
| Water, deionized | 45.8 | 46.2 | 46.7 | 47.2 | 45.2 | 44.7 |
| Ethanol USP (200 proof) | 43.5 | 43.5 | 43.5 | 43.5 | 43.5 | 43.5 |
| Hydroxypropyl guar hydroxypropyl trimonium chloride[2] | 2.4 | 2.0 | 1.5 | 1.0 | 3.0 | 3.5 |
| Acetic acid | 3.6 | 3.6 | 3.6 | 3.6 | 3.6 | 3.6 |
| Water/Ethanol | 1.053 | 1.062 | 1.074 | 1.085 | 1.039 | 1.028 |
| Acetic acid/Ethanol | 0.083 | 0.083 | 0.083 | 0.083 | 0.083 | 0.083 |
| TOTAL | 100.0 | 100.0 | 100.0 | 100.0 | 100.0 | 100.0 |

[1]Schercemol LL ester
[2]Jaguar C162; CAS No. 71329-50-5; DS 0.10; MS 0.6; contains 11/5% w/w water

TABLE 25

Terbinafine HCl Compositions Containing Different Amounts of Cationic Guar Gum

| | Composition | | | | | |
|---|---|---|---|---|---|---|
| Time | R | AI | AJ | AK | AL | AM |
| At 0 hr | clear gel | clear gel | clear gel | clear gel | clear gel | clear gel |
| After 1 week | clear gel | clear gel | clear gel | clear gel | clear gel | clear gel |

TABLE 26

Viscosity Results

| | Composition | | | | | |
|---|---|---|---|---|---|---|
| | R | AI | AJ | AK | AL | AM |
| Viscosity (cP) | 2361 | 1533.0 | 704.2 | 207.1 | 4929.0 | 7042.0 |
| Torque (%) | 5.7 | 3.7 | 1.7 | 0.5 | 11.9 | 17.0 |

Terbinafine hydrochloride compositions containing different amounts of acetic acid were investigated, the appearance thereof noted, and viscosity measured as described hereinabove. The prepared compositions, the noted appearance and measured viscosity are shown in Tables 27, 28 and 29, below.

TABLE 27

Terbinafine HCl Compositions With Different Amounts of Acetic Acid

| Ingredient, wt.-% | Composition | | | | | | |
|---|---|---|---|---|---|---|---|
| | R | AN | AO | AP | AQ | AR | AS |
| Terbinafine HCl | 1.2 | 1.2 | 1.2 | 1.2 | 1.2 | 1.2 | 1.2 |
| Lauryl lactate[1] | 3.5 | 3.5 | 3.5 | 3.5 | 3.5 | 3.5 | 3.5 |
| Water, deionized | 45.8 | 45.8 | 45.8 | 45.8 | 45.8 | 45.8 | 45.8 |
| Ethanol USP (200 proof) | 43.5 | 46.1 | 45.1 | 44.1 | 43.1 | 42.1 | 47.1 |
| Hydroxypropyl guar hydroxypropyl trimonium chloride[2] | 2.4 | 2.4 | 2.4 | 2.4 | 2.4 | 2.4 | 2.4 |
| Acetic acid | 3.6 | 1 | 2 | 3 | 4 | 5 | 0 |
| Water/Ethanol | 1.053 | 0.994 | 1.016 | 1.039 | 1.063 | 1.088 | 0.972 |
| Acetic acid/Ethanol | 0.083 | 0.022 | 0.044 | 0.068 | 0.093 | 0.119 | 0 |
| TOTAL | 100.0 | 100.0 | 100.0 | 100.0 | 100.0 | 100.0 | 100.0 |

[1]Schercemol LL ester
[2]Jaguar C162; CAS No. 71329-50-5; DS 0.10; MS 0.6; contains 11/5% w/w water

TABLE 28

Terbinafine HCl Compositions Containing Different Amounts of Acetic Acid

| Time | Composition | | | | | | |
|---|---|---|---|---|---|---|---|
| | R | AN | AO | AP | AQ | AR | AS |
| At 0 hr | clear gel | very slightly opaque gel | clear gel | clear gel | clear gel | clear gel. | slightly opaque gel |
| After 1 week | clear gel | very slightly opaque gel | clear gel | clear gel | clear gel | clear gel | slightly opaque gel |

TABLE 29

Viscosity Results

| | Composition | | | | | | |
|---|---|---|---|---|---|---|---|
| | R | AN | AO | AP | AQ | AR | AS |
| Viscosity (cP) | 2361 | 2610 | 2651 | 2568 | 2610 | 2693 | 2568 |
| Torque (%) | 5.7 | 6.3 | 6.4 | 6.2 | 6.3 | 6.5 | 6.2 |

Topical antifungal compositions containing an azole as the antifungal agent are illustrated in Table 30, below.

TABLE 30

Topical Antifungal Azole Compositions

| Ingredient | Amount, wt.-% | |
|---|---|---|
| | EA | EB |
| Efinaconazole | 2.0 | 2.0 |
| Lauryl lactate[1] | 2.7 | 2.7 |
| Water, deionized | 48.0 | 48.0 |
| Ethyl alcohol USP (200 proof) | 42.6 | 42.6 |
| Lactic acid | 2.7 | 0 |
| Acetic acid | 0 | 2.7 |
| Hydroxypropyl guar hydroxypropyl trimonium chloride[2] | 2.0 | 2.0 |
| Water/Ethanol | 1.13 | 1.13 |
| Acid/Ethanol | 0.063 | 0.063 |
| TOTAL | 100 | 100 |

[1]Schercemol LL ester
[2]Jaguar C162; CAS No. 71329-50-5; DS 0.10; MS 0.6; contains 11.5% w/w water A skin permeation study was performed using the compositions shown in Table 30, above. Cadaver back skin (52-year old male) was used in a Franz cell (3.65 ml volume, 0.55 cm² surface area) with heating/stirring blocks and at a temperature of 35° C. Receptor compartment contained saline with sodium azide (pH 5.5). Three or four replicates (25 µl and a 25 mg control) were prepared. Sampling volume was 300 µL. Fresh buffer was replaced after each sample removal. Sampling was carried out at 2, 4, 6 and 24 hours. The obtained samples were assayed using high performance liquid chromatography (HPLC). The control was a commercially available, efinaconazole containing cream (10%), Jublia® cream, Dow Pharmaceutical Sciences, Inc., Petaluma, CA, having the following composition:
  efinaconazole, 10 wt.-%
  EDTA disodium, 0.00025 wt.-%
  water, 1 wt.-%
  diisopropyl adipate, 12 wt.-%
  cyclomethicone, 13 wt.-%
  citric acid, anhydrous, 0.1 wt.-%
  butylated hydroxytoluene (BHT), 0.1 wt.-%
  C12-C15 alkyl lactate, 10 wt.-%
  ethanol, 53.8 wt.-%
The obtained permeation profiles for the compositions of Table 30 are presented in Table 31, below, and in FIG. 10.

TABLE 31

Permeation Data

| Time, | Cumulative Amount in Receptor, μg/cm² | | | | | |
|---|---|---|---|---|---|---|
| | Efinaconazole | | | | Jublia ® | |
| Hrs. | EA | ±SD | EB | ±SD | Cream | ±SD |
| 2 | 48.83 | 38.47 | 28.73 | 5.58 | 0 | 0 |
| 4 | 99.35 | 101.21 | 69.37 | 42.61 | 1.22 | 2.73 |
| 6 | 152.05 | 96.06 | 116.19 | 61.50 | 3.30 | 5.08 |
| 24 | 306.53 | 86.56 | 219.44 | 64.04 | 19.08 | 22.65 |

The foregoing data show enhanced permeation of efinaconazole as compared to a commercially available preparation containing the same active ingredient albeit at a five-fold higher concentration.

The foregoing discussion and the examples are illustrative and are not to be taken as limiting. Still other variants within the spirit and scope of the invention are possible and will readily present themselves to those skilled in the art.

The invention claimed is:

1. A topical gel composition which comprises an antifungal agent selected from the group consisting of terbinafine, amorolfine, and efinaconazole, a lactate ester of a $C_2$ to $C_{16}$ saturated aliphatic alcohol, an organic acid having a pKa value in the range of about 3.8 to about 5, ethanol, water, and a cationic galactomannan gum.

2. The composition in accordance with claim 1 wherein the antifungal agent is an allylamine selected from the group consisting of terbinafine and amorolfine.

3. The composition in accordance with claim 1 wherein the terbinafine is terbinafine hydrochloride.

4. The composition in accordance with claim 1 wherein the amorolfine is amorolfine hydrochloride.

5. The composition in accordance with claim 1 wherein the organic acid is acetic acid.

6. The composition in accordance with claim 1 wherein the cationic galactomannan gum is a cationic polygalactomannan gum ether salt.

7. The composition in accordance with claim 6 wherein the cationic polygalactomannan gum ether salt is hydroxypropyl guar hydroxypropyl trimonium chloride.

8. The composition in accordance with claim 7 wherein the hydroxypropyl guar hydroxypropyl trimonium chloride has a DS value in the range of about 0.07 to about 2 and a MS value in the range of about 0.4 to about 0.8.

9. The composition in accordance with claim 7 wherein the hydroxypropyl guar hydroxypropyl trimonium chloride has a DS value of about 0.10 and a MS value of about 0.6.

10. The composition in accordance with claim 1 comprising, based on the total weight of the composition, about 0.5 to about 3 percent by weight terbinafine, about 1 to about 5 percent by weight lactate ester of a $C_2$ to $C_{16}$ saturated aliphatic alcohol, about 0.5 to about 5 percent by weight of organic acid, about 35 to about 55 percent by weight ethanol, about 35 to about 55 percent by weight water, and about 1 to about 3 percent by weight hydroxypropyl guar hydroxypropyl trimonium chloride.

11. The composition in accordance with claim 1 comprising, based on the total weight of the composition, about 1.2 percent by weight terbinafine, about 3.5 percent by weight lactate ester of a $C_2$ to $C_{16}$ saturated aliphatic alcohol, about 1 to about 4 percent by weight organic acid, about 40 to about 50 percent by weight ethanol, about 40 to about 50 percent by weight water, and about 2 to about 2.5 percent by weight hydroxypropyl guar hydroxypropyl trimonium chloride.

12. The composition in accordance with claim 2 and having a water-to-ethanol weight ratio in the range of about 1 to about 1.1 and an organic acid-to-ethanol weight ratio in the range of about 0.04 to about 0.09.

13. The composition in accordance with claim 12 wherein the antifungal agent is terbinafine hydrochloride.

14. The composition in accordance with claim 12 wherein the antifungal agent is amorolfine hydrochloride.

15. The composition in accordance with claim 1 wherein the antifungal agent is efinaconazole.

16. The composition in accordance with claim 15 comprising, based on the total weight of the composition, about 2 percent by weight efinaconazole, about 2.7 percent by weight lauryl lactate, about 2.7 percent by weight acetic acid, about 42.6 percent by weight ethanol, about 48 percent by weight water, and about 2 percent by weight hydroxypropyl guar hydroxypropyl trimonium chloride.

* * * * *